United States Patent
La Droitte et al.

(12) 
(10) Patent No.: US 6,544,568 B2
(45) Date of Patent: *Apr. 8, 2003

(54) SYMBIOTIC FUNCTIONAL FOOD CONTAINING LACTIC ACID BACTERIA

(75) Inventors: Philippe La Droitte, Revel (FR); Claudio De Simone, Ardea (IT)

(73) Assignee: VSL Pharmaceuticals Inc., Gaithersburg, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/461,602

(22) Filed: Dec. 15, 1999

(65) Prior Publication Data

US 2002/0044990 A1 Apr. 18, 2002

(30) Foreign Application Priority Data

Dec. 15, 1998 (IT) ............................... MI98A2692

(51) Int. Cl.⁷ ............................. A21D 13/08; A61P 1/00
(52) U.S. Cl. ........................................ 426/61; 424/93.45
(58) Field of Search ................... 426/61, 601, 330.6, 426/613, 33, 659, 572, 653, 93.45

(56) References Cited

U.S. PATENT DOCUMENTS

| 5,716,615 A | 2/1998 | Cavaliere Vasely et al. ............... 424/93.4 |
| 5,968,569 A | * 10/1999 | Cavaldini et al. .............. 426/61 |
| 6,399,124 B1 | * 6/2002 | Lesens et al. .................. 426/61 |

FOREIGN PATENT DOCUMENTS

| EP | 0872186 | 10/1993 |
| EP | 0704164 | 9/1995 |
| JP | 62061572 | 3/1987 |
| JP | 02200639 | 8/1999 |
| WO | 97/16077 | 11/1999 |

OTHER PUBLICATIONS

I. Garard, Introductory Food Chemistry, AVI Pub. Inc., p. 21–22, Jan. 1976.*

* cited by examiner

*Primary Examiner*—Keith Hendricks
(74) *Attorney, Agent, or Firm*—Nixon & Vanderhye P.C.

(57) ABSTRACT

The present invention relates to a functional food/health food in the form of a baked good comprising a non-baked fat-based composition and a baked part, characterized in that the fat-based composition is essentially water-free and comprises live lyophilized lactic bacteria and in that the baked part comprises one or more non-digestible fiber-like substances. Also provided are intermediates thereof, a method for its production and its use.

17 Claims, No Drawings

SYMBIOTIC FUNCTIONAL FOOD CONTAINING LACTIC ACID BACTERIA

The present invention generally relates to a functional food/health food which comprises both a probiotic and a prebiotic component, to intermediates thereof, to a method for its production and to its use.

Probiotics are live microbial food supplements which beneficially affect the host by improving its intestinal microbial balance. Nowadays, a number of different bacteria are used as probiotics. In human foods, the bacteria are mainly incorporated into fermented milk products such as yogurts. To be effective, a probiotic must survive for the lifetime of the product. This is why the majority of probiotic food products, like fermented milk products, have a short shelf life.

Prebiotics are non-living, non-digestible food ingredients that beneficially affect the host by selectively stimulating the growth and/or activity of one or a limited number of bacteria, including probiotic bacteria, in the colon, with the effect of improving the host's health.

The present invention foresees a functional food/health food with a long shelf life at non-refrigerated temperatures which comprises both probiotics and prebiotics (also referred to herein as "symbiotic"). What is claimed is a baked good comprising a non-baked fat-based composition and a baked part, characterised in that the fat-based composition is essentially water-free and comprises live lyophilized lactic bacteria and in that the baked part comprises one or more non-digestible fibre-like substances.

One of the advantages of the baked good of the invention is that the non-digestible fibre-like substance is added to the baked part. This allows an effective amount of non-digestible fibre-like substance to be added to the product without technical problems such as problems with the texture of the fat-based composition and without unduly influencing the taste and appearance of the product. An effective amount of non-digestible fibre-like substance is an amount which provides the desired fibre-like function in the body, i.e. a daily dosage of 2 to 15 g of non-digestible fibre-like substance.

To show good survivability in the baked good, the bacteria are lyophilized and formulated into an essentially water-free environment. Preferably the water activity ($A_w$) of the fat-based composition is less than 0.6, particularly preferred it is in the range of 0.2 to 0.6, more particularly preferred it is between 0.35 and 0.45.

It was found by the present inventors that shortenings with a melting point higher than 30° C. are optimal carriers of lactic bacteria, when long term storage at non-refrigerated temperatures is required. In particular it has been found that, even though an initial loss of viability of a factor of 100 is found, following the initial loss, a stabilization of the viability of the bacteria is achieved, even at temperatures exceeding 30° C. Accordingly, the fat-based composition comprises preferably a type of shortening with a melting point higher than 30° C. Examples of such shortenings are palm oil, palm kernel oil, coconut oil, cocoa butter, peanut butter or other vegetable butters, butter, margarine, hydrogenated or partially hydrogenated vegetable oils and/or vegetable oils, alone or mixed, whereby palm oil is preferred.

Typically, the fat-based composition contains 10 to 40 wt % of shortening, preferably 25 to 35 wt % based on the total weight of the fat-based composition.

Suitable lactic bacteria are selected from the genera Lactobacillus, Lactococcus, Bifidobacterium and Streptococcus, whereby they are preferably employed in form of a mix of more than one lactic bacteria type. Preferred lactic bacteria belong to the species *Streptococcus thermophilus* and/or *Lactobacillus acidophilus*. Preferably, at least one member of each of these two species is used in the fat-based composition of the invention. Members of the species *Streptococcus thermophilus* and *Lactobacillus acidophilus* are particularly resistant against hydrochloric acid, which is an indication for good survival in the stomach. Particularly preferred lactic bacteria according to the invention are the strains *Streptococcus thermophilus* ATCC 19258 and *Lactobacillus acidophilus* ATCC 314 (ATCC—American Type Culture Collection, 12301 Parklawn Drive, Rockville, Md. 20852, USA). Other lactic bacteria strains which can be used according to the invention include *Bifidobacterium longum* ATCC 15707, *Lactobacillus casei* ATCC 25180, *Bifidobacterium bifidum* ATCC 11863, *Bifidobacterium infantis* ATCC 15697, *Lactobacillus plantarum* ATCC 8014 and *Lactobacillus delbrueckii* subsp. *bulgaricus* ATCC 7994.

Typically, the fat-based composition contains 1 to 10 wt % of lyophilized bacteria, preferably 4 to 6 wt % based on the total weight of the fat-based composition. The concentration of lactic bacteria typically lies in the range of $10^6$ to $10^{12}$ CFUs/g of fat-based composition, preferably it lies in the range of $10^7$ to $0.5 \times 10^{12}$, more preferably in the range of $10^9$ to $10^{11}$, particularly preferred in the range of $0.5 \times 10^{10}$ to $1.5 \times 10^{10}$ CFUs/g, more particularly preferred is about $10^{10}$ CFUs/g.

The fat-based composition typically contains of one or more of the following ingredients in addition to the lactic bacteria and the shortening:

sucrose, dextrose, fructose, dried honey, dried fruits sugars, oligosaccharides, vegetable fibers, full cream or skimmed milk powder, milk proteins, vegetable starch, flour or protein, cocoa powder, nuts, chocolate, coffee, vanilla, lecithin, salt, flavors, colors.

Preferably, the fat-based composition contains 50 to 89 wt % of one or more of the additional ingredients listed in the previous paragraph, particularly 59 to 71 wt % based on the total weight of the fat-based composition.

The fat-based composition may be a filling and/or a coating of the baked part. Preferably it is a filling.

A preferred fat-based composition comprises in addition to the lactic bacteria as set out above sugar, palm oil, skim milk powder and a flavoring agent.

The baked good according to the invention may be a cream sandwich biscuit, a tartlet or pastry, etc. Preferably it is a cream sandwich biscuit.

Suitable non-digestible fibre-like substances include oligosaccharides such as fructo-oligosaccharides, galacto-oligosaccharides, soy-oligosaccharides, xylo-oligosaccharides and isomalto-oligosaccharides, whereby fructo-oligosaccharides (with less than 5 sugars) and/or xylo-oligosaccharides are preferred.

Typically, the baked part contains 10 to 30 wt % of non-digestible fibre-like substances, preferably 15 to 25 wt % based on the total weight of the baked part.

Apart from the non-digestible fibre-like substances the baked part typically comprises one or more of the following ingredients: wheat flour, vegetable starch, flour or protein, shortening, sugars, full cream or skimmed milk powders, milk protein, leavening agents, salt, flavours, fruits, cocoa, chocolate, nuts, water, etc.

Typically, the baked part contains 70 to 90 wt % of one or more of the additional ingredients set out in the preceding paragraph, preferably 75 to 85 wt % based on the total weight of the baked part.

The weight ratio in the baked good of the invention of the baked part to the fat-based composition lies typically between 9:1 to 6:4, preferably 8:2 to 6:3.

The baked good of the invention provides a daily dosage of 2 to 15 g, preferably 3 to 10 g, particularly preferred about 5 g of the non-digestible fibre-like substance. The daily ration of lactic bacteria is from of $5\times10^8$ to $1\times10^{12}$ CFU (colony forming units), preferably $1\times10^9$ to $5\times10^{11}$ CFU, particularly preferred about $10^{11}$ CFU of lactic bacteria.

The baked good of the invention preferably has a shelf life of at least six months at room temperature (18–22° C.). Unlike known products containing lactic bacteria, the baked good of the invention does not need to be stored refrigerated.

The invention further provides a fat-based composition comprising live lyophilized lactic bacteria in a concentration of $10^6$ to $10^{12}$, preferably $10^7$ to $0.5\times10^{12}$, more preferably $10^9$ to $10^{11}$, particularly preferred $0.5\times10^{10}$ to $1.5\times10^{10}$, more particularly preferred about $10^{10}$ CFUs/g of fat-based composition, and at least one shortening with a melting point higher than 30° C. at a concentration of 10–40 wt % of the total weight of the composition. Preferably the lyophilized lactic bacteria is selected from the species *Streptococcus thermophilus* and *Lactobacillus acidophilus* and preferably is composed of at least one member of the species *Streptococcus thermophilus* and at least one member of the species *Lactobacillus acidophilus*.

Particularly preferred the member of the species *Streptococcus thermophilus* is *Streptococcus thermopilus* ATCC 19258 and the member of the species *Lactobacillus acidophilus* is *Lactobacillus acidophilus* ATCC 314.

The fat-based composition of the invention apart from being useful as the non-baked part of the baked good, can also be used independently as a spread (i.e. such as butter, margarine, chocolate spread, peanut butter, etc.).

Also provided is a process for producing the baked good of the invention comprising the steps of:

mixing together the ingredients of the fat-based composition without heating above 40° C., mixing together the ingredients of the baked part and baking same, and combining the baked part and the fat-based composition.

Lactic bacteria play several important roles in the gastrointestinal tract, such as:

1) Production of nutrients for colonic mucosa: acetate, butyrates, propionate, other short chain fatty acids, pyruvate, lactate, and amino acids such as arginine, cysteine and glutamine;
2) Production of nutrients: the B group vitamins and folic acid, antioxidants and polyamines, histamine, 5-hydroxytryptamine, piperidine, tyramine, cadaverine, pyrrolidine, etc.;
3) Elimination of toxins and unwanted substances;
4) Regulation of digestive function: mucus utilization, nutrient absorption; gastrointestinal motility, blood flow, gastrointestinal hormone secretion;
5) Host's protection against potential pathogenic microorganisms;
6) Stimulation of the immune system.

The fat-based composition per se and in particular the baked good of the invention are effective in maintaining a healthy gut function and in restoring or promoting a healthy balance of gut bacteria which can help to improve digestive regularity and health and which in particular reduces incidence of constipation and diarrhea. The probiotic component of the compositions may outcompete harmful bacteria for growth in the intestines, thereby reducing toxic effects on the digestive process. Furthermore, colonisation of the gut with beneficial lactic bacteria flora may in itself stimulate the digestive system and improve bowel control. These two effects both contribute to a reduction in the frequency, recurrence, severity, and duration of attacks of diarrhea or constipation. When consumed regularly the compositions of the invention reduce the risk that an individual will develop chronic symptoms, namely clinical disorders of the bowel.

The fat-based composition and the baked good of the invention are generally effective for the prevention and treatment of gastrointestinal functional or organic disorders including irritable bowel syndrome (IBS), in isolation or in combination with conventional treatments of any nature. The requirement for medical intervention, other than dietary intervention in the form of administration of the baked good or fat-based composition of the invention, may vary between cases, depending on the severity of symptoms. The compositions are furthermore effective for stimulating the immune system, for promoting resistance to infection, for controlling the pH in the colon, for controlling colonic motion and transit time, as anti-carcinogenic and anti-mutagenic agents, and in having hypocholesterolemic action. The fat-based composition per se and in particular the baked good are preferably used for the prevention and/or treatment of constipation and diarrhea.

We have found that patients with any form of Functional Bowel Disorder (FBD) are liable to benefit from consuming the baked good or fat-based composition of the invention. FBD is a general term for a range of gastrointestinal disorders which are chronic or semi-chronic and which are associated with bowel pain, disturbed bowel function and social disruption. Particular combinations and prevalence of symptoms characterize the following seven FBD subgroups, which are defined in accordance with the classification system known as the "Rome criteria":

1) C1: Constipation-predominant Irritable Bowel Syndrome
2) C1: Diarrhea-predominant Irritable Bowel Syndrome
3) C3: Functional constipation
4) C4: Functional diarrhea
5) C2: Functional abdominal bloating
6) F3a: Pelvic Floor dyssynergia
7) F3b: Internal Anal Sphincter Dysfunction Patients who can be assigned to any of these universally recognised sub-groups will observe an improvement in their symptoms following ingestion of the biscuits or fat-based compositions of the invention. In particular, those patients whose symptoms fall into sub-groups 1) to 4) above can expect a marked positive outcome.

Any medical practitioner with a good knowledge of gastroenterology can categorise patients into these groups. For example, C1: Irritable Bowel Syndrome is characterised by at least 3 continuous months or recurrent symptoms of:

1. abdominal pain or discomfort which is
   (a) relieved with defecation,
   (b) and/or associated with a change in frequency of stool,
   (c) and/or associated with a change in consistency of stool; and
2. two or more of the following, on at least a quarter of occasion or days;
   (a) altered stool frequency,
   (b) altered stool form (lumpy/hard or loose/watery),
   (c) altered stool passage (straining, urgency, or feeling of incomplete evacuation),
   (d) passage of mucus,
   (e) bloating or feeling of abdominal distention.

C3: Functional Constipation is defined by two or more of the following symptoms for at least 3 months:

1. straining at defecation at least a quarter of the time
2. lumpy and/or hard stools at least a quarter of the time
3. sensation of incomplete evacuation at least a quarter of the time
4. two or fewer spontaneous bowel movements in a week Abdominal pain is not required, loose stools are not present, and there are insufficient criteria for IBS. These criteria may not apply when the patient is taking laxatives.

C4: Functional Diarrhea is characterized by two or more of the following symptoms for at least 3 months:
1. unformed (mushy or watery) stool more than three quarters of the time,
2. three or more bowel movements per day greater than half the time, and
3. increased stool bowel as compared to the community norm (>200 g/day for North Americans and Europeans) but no more than 500 g per day. There are insufficient criteria for IBS. Abdominal pain is not complained of, and hard or lumpy stools are not present. Urgency is a prominent symptom and fecal incontinence or soiling may occur.

Similarly, C2: Functional abdominal bloating is typified by symptoms of abdominal fullness, bloating or distention. F3a: Pelvic Floor Dyssynergia is characterised by straining and a feeling of incomplete evacuation. F3b: Internal Anal Sphincter Dysfunction is diagnosed by F3a symptoms together with manometric tests.

The invention will be further illustrated by the following examples.

EXAMPLES

Example 1

A Symbiotic Biscuit (Made Up of 10 g of filling and 26 g of Biscuit)

Filling—The following ingredients are mixed at room temperature. Percentages are weight percentages, based on the total filling weight.

| | |
|---|---|
| sugar | 40% |
| palm oil | 31% |
| skim milk powder | 24% |
| bacteria mix | 5% (figures rounded up to the nearest percentage) |
| aroma | 0.07% |

The bacterial content of two filled biscuits/day (36 g) consists of

| | |
|---|---|
| *Streptococcus thermophilus*: | $0.5 \times 10^{11}$ CFU |
| *Lactobacillus acidophilus*: | $0.5 \times 10^{11}$ CFU |

Biscuit part—The following ingredients are mixed and baked. Percentages are weight percentages, based on the total biscuit part weight.

| | % |
|---|---|
| prebiotic | 19.3 |
| wheat flour | 56 |
| palm oil | 15.4 |
| soy flour | 2.3 |

-continued

| | % |
|---|---|
| skimmed milk powder | 2.1 |
| leavening agents | 0.5 |
| salt | 0.2 |
| flavors | 0.1 |
| water | 4.1 |

The prebiotic content of two filled biscuits/day (36 g) consists of short chain fructo-oligosaccharides ((glucose-fructose)$_n$– n<5) 5 g/day.

The recommended daily ration is two filled biscuits (36 g) per day.

Comparative Example 1

(Placebo Biscuit)

Filling—The following ingredients are mixed at room temperature. Percentages are weight percentages, based on the total filling weight.

| | |
|---|---|
| Sugar | 40% |
| Palm oil | 31% |
| Skim milk powder | 29% (figures rounded up to the nearest percentage) |
| Aroma | 0.07% |

Biscuit Part—The following ingredient were mixed and baked. Percentages are weight percentages, based on the total biscuit weight.

| | |
|---|---|
| Wheat flour | 54% |
| Cane Sugar | 15.6% |
| Palm oil | 15.4% |
| Yeast | 2.7% |
| Soy flour | 2.2% |
| Skimmed milk powder | 2.1% |
| Coconut powder | 1.2% |
| Leavening agents | 0.5% |
| Salt | 0.2% |
| Flavours | 0.1% |
| Water | 6% |

The recommended daily ration is two filled biscuits (36 g) per day.

Example 2

Resistance of Bacteria Mix Against Hydrochloric Acid

The resistance of a mix of the two lactic bacteria strains, *S. thermophilus* ATCC 19258 at a concentration of $7.4 \times 10^{11}$ and *L. acidophilus*. ATCC 314 at a concentration of $2.0 \times 10^{11}$, is tested against hydrochloric acid in vitro. After 3 hours of incubation at pH 3.3 and 37° C. the viability decreases only one order of magnitude. This in vitro resistance to hydrochloric acid provides a good indication that these two strains will also show good survival in the stomach (where a pH of less than 3 is only present in fasting individuals). Moreover a better survival of the bacteria is observed when the lactic bacteria are introduced in a buffered system like the present food.

Example 3

Bacteria Survival in Simulation of Storage and Transport

Stability during storage and transport of a bacteria mix containing *S. thermophilus* and *L-acidophilus* is tested as follows:

| added amount in 2 biscuits | biscuits 12 h at 40° C.* | biscuits 30 days at 30° C.** | biscuits 6 months at room T |
|---|---|---|---|
| $1.4 \times 10^{11}$ CFU | $4 \times 10^{10}$ CFU | $3 \times 10^{10}$ CFU | $1.8 \times 10^{10}$ CFU |

*simulation of a transport in summer
**simulation of a storage in summer

These results show a very good storage and transport survival at unfavorable temperature conditions and a shelf life of at least 6 months at room temperature.

Example 4

Clinical Study

A double blind versus placebo study involving 60 patients with Intestinal Function Disorders is carried out. Selected patients with constipation or diarrhea belonging to the following sub-groups of the Rome classification of Intestinal Functional Disorders: Irritable Bowel Syndrome, Functional Abdominal Bloating, Functional Diarrhea, are divided into four groups:

- patients with constipation receiving placebo biscuit of Comparative Example 1
- patients with constipation receiving the symbiotic biscuit of Example 1
- patients with diarrhea receiving placebo biscuit of Comparative Example 1
- patients with diarrhea receiving the symbiotic biscuit of Example 1

In each group, patients are matched for sex, symptoms severity and for Functional Disorder sub-group diagnosis.

After a 3 week run in period during which clinical and instrumental examinations are performed, the patients are enrolled in a 4 week nutritional intervention.

Exclusion criteria include simultaneous administration of antibiotics, drugs having an effect on gastro-intestinal motion, age<18 years and >70 years and pregnancy.

Main parameters measured are:
- 11 clinical parameters (feeling of urgency, feeling of incomplete evacuation, feeling of abdominal distention, abdominal pain, etc . . . )
- microbiological analysis of fecal samples for total aerobes and anaerobes and for Bifidobacteria, Lactobacilli and *S thermophilus*.
- total and segmental transit time evaluated by means of radio-opaque marker ingestion and the execution of X-ray films of the abdomen.
- complete colonic and anorectal motor activity explored by means of a manometric probe introduced up to the hepatic flexure.

Results:

The majority of patients having diarrhea and colonic constipation reported improvements in their symptoms upon taking the biscuit of Example 1. That is, total intestinal transit time decreased in patients with colonic constipation and was accompanied by increased evacuation frequency. Conversely, patients suffering from diarrhea tended to experience a decrease in evacuation frequency. In comparison, subjects of the study who received the placebo biscuit made as described in Comparative Example 1 were significantly less likely to report marked relief from their symptoms.

Therefore, with reference to the FBD Rome classification system, patients falling into the following groups experienced the greatest relief from their symptoms following consumption of the baked biscuit of the invention:

C1: Constipation-predominant Irritable Bowel Syndrome
C1: Diarrhea-predominant Irritable Bowel Syndrome
C3: Functional constipation
C4: Functional diarrhea

What is claimed is:

1. A food for humans consisting essentially of:
   (a) a pair of baked parts comprising a non-digestible fiber, and between them
   (b) a non-baked part comprising a fat-based component which has a melting point greater than 30° C. and contains live lyophilized lactic acid bacteria selected from the group consisting of Lactobacillus, Bifidobacterium and Streptococcus, and mixtures thereof,
   wherein the lactic acid bacteria in the fat-based component remain viable for at least six months at room temperature.

2. The food according to claim 1, wherein the lactic acid bacteria are selected from *Streptococcus thermophilis, Lactobacillus acidophilus* and mixtures thereof.

3. The food according to claim 1, comprising at least one strain of the species *Streptococcus thermophilus* and at least one strain of the species *Lactobacillus acidophilus*.

4. The food according to claim 1, comprising at least one strain of the species *Streptococcus thermophilus* and at least one strain of the species *Lactobacillus acidophilus* and at least another bacterium belonging to the group of Lactobacilli, Bifidobacteria or both.

5. The food according to claim 4, wherein the non-digestible fiber is selected from the group consisting of fructo-oligosaccharides, galacto-oligosaccharides, soy-oligosaccharides, xylo-oligosaccharides, isomalto-oligosaccharides, and mixtures thereof.

6. The food according to claim 5, wherein the baked part is in a biscuit form providing about 5 g of the non-digestible fiber and the non-baked part comprises a fat-based component which provides about $1 \times 10^9$ CPU of lactic acid bacteria.

7. The food according to claim 1, wherein the non-digestible fiber is selected from the group consisting of short chain and long chain oligosaccharides, and mixtures thereof.

8. The food according to claim 1, wherein the non-baked part further comprises one or more of a digestible sugar, skim milk powder or a flavoring agent.

9. The food according to claim 1, wherein the baked part is in a biscuit form that provides 2 to 15 g of the non-digestible fiber and the non-baked part comprises a fat-based component comprising from $5 \times 10^8$ to $1 \times 10^{12}$ CFU of lactic acid bacteria.

10. The food according to claim 1, wherein the bacteria content is at least $1.8 \times 10^{10}$ CPU after storage at 11–22° C. for 30 days.

11. The food according to claim 1, wherein the baked part is in a biscuit form providing 3 to 10 g of the non-digestible fiber and the non-baked part is between the two biscuits and comprises a fat-based component comprising $1 \times 10^9$ to $5 \times 10^{11}$ CPU of lactic acid bacteria.

12. The food according to claim 1, wherein the concentration of live lyophilized lactic acid bacteria is $1 \times 10^9$ to $5 \times 10^{11}$ CFU/g of the fat-based component.

13. A method of preventing or treating a functional bowel disorder comprising administering to a human patient in need of such treatment an effective amount of the food of claim 1.

14. A process for producing a food for humans according to claim 1, comprising the steps of:
   (a) mixing together ingredients comprising the non-baked part comprising the fat-based component without heating above 40° C.,
   (b) mixing together the non-digestible fiber with ingredients comprising the baked part and baking same, and
   (c) placing the non-baked part between a pair of the baked parts.

15. The food according to claim 1, wherein the fat in the fat-based component is a vegetable oil.

16. The food according to claim 15, wherein the vegetable oil is selected from the group consisting of palm oil, cocoa butter, peanut butter, vegetable butter, margarine and mixtures thereof.

17. The food according to claim 16, wherein the vegetable oil is palm oil.

* * * * *

UNITED STATES PATENT AND TRADEMARK OFFICE
CERTIFICATE OF CORRECTION

PATENT NO. : 6,544,568 B2
DATED : April 8, 2003
INVENTOR(S) : La Droitte et al.

It is certified that error appears in the above-identified patent and that said Letters Patent is hereby corrected as shown below:

<u>Title page,</u>
Item [73], should read as follows:
-- [73] Assignee:     Mendes s.r.l.,
                        Rome, Italy

VSL Pharmaceuticals, Inc.
                        Gaithersburg, MD (US) --

Signed and Sealed this

Twenty-sixth Day of August, 2003

JAMES E. ROGAN
*Director of the United States Patent and Trademark Office*